(12) United States Patent
Pengpanich et al.

(10) Patent No.: US 10,851,230 B2
(45) Date of Patent: Dec. 1, 2020

(54) ION EXCHANGE RESIN FOR PRODUCING BISPHENOL, AND A METHOD FOR PRODUCING BISPHENOL USING SAID ION EXCHANGE RESIN

(71) Applicant: PTT Global Chemical Public Company Limited, Bangkok (TH)

(72) Inventors: Sitthiphong Pengpanich, Chatuchak Bangkok (TH); Papapida Pornsuriyasak, Chatuchak Bangkok (TH); Suchada Tang-Amornsuksan, Chatuchak Bangkok (TH)

(73) Assignee: PTT GLOBAL CHEMICAL PUBLIC COMPANY Limited, Bangkok (TH)

( * ) Notice: Subject to any disclaimer, the term of this patent is extended or adjusted under 35 U.S.C. 154(b) by 0 days.

(21) Appl. No.: 16/060,162

(22) PCT Filed: Oct. 31, 2016

(86) PCT No.: PCT/TH2016/000088
§ 371 (c)(1),
(2) Date: Jun. 7, 2018

(87) PCT Pub. No.: WO2017/099674
PCT Pub. Date: Jun. 15, 2017

(65) Prior Publication Data
US 2018/0355159 A1 Dec. 13, 2018

(30) Foreign Application Priority Data
Dec. 9, 2015 (TH) .................................. 1501007417

(51) Int. Cl.
| | |
|---|---|
| *C08L 25/08* | (2006.01) |
| *B01J 31/30* | (2006.01) |
| *B01J 39/00* | (2006.01) |
| *C07C 37/20* | (2006.01) |
| *C08F 8/34* | (2006.01) |
| *C08F 8/30* | (2006.01) |
| *B01J 31/08* | (2006.01) |
| *B01J 39/20* | (2006.01) |
| *C07C 39/16* | (2006.01) |
| *C08K 5/17* | (2006.01) |
| *C08K 5/3432* | (2006.01) |
| *C08F 212/08* | (2006.01) |
| *C08F 212/36* | (2006.01) |

(52) U.S. Cl.
CPC .............. *C08L 25/08* (2013.01); *B01J 31/08* (2013.01); *B01J 39/20* (2013.01); *C07C 37/20* (2013.01); *C07C 39/16* (2013.01); *C08F 8/30* (2013.01); *C08F 8/34* (2013.01); *C08K 5/17* (2013.01); *C08K 5/3432* (2013.01); *B01J 2231/347* (2013.01); *C08F 212/08* (2013.01); *C08F 212/36* (2013.01)

(58) Field of Classification Search
None
See application file for complete search history.

(56) References Cited

U.S. PATENT DOCUMENTS

| | | |
|---|---|---|
| 2,597,438 A | 5/1952 | Bodamer |
| 3,394,089 A | 7/1968 | Mcnutt et al. |
| | (Continued) | |

FOREIGN PATENT DOCUMENTS

CN 101585849 A 11/2009

OTHER PUBLICATIONS

Rohm "Amberjet™ 1200 H Industrial Grade Strong Acid Cation Exchanger", 2019, pp. 1-2 (Year: 2019).*

(Continued)

*Primary Examiner* — Medhanit W Bahta
(74) *Attorney, Agent, or Firm* — Troutman Pepper Hamilton Sanders LLP

(57) ABSTRACT

This invention relates to an ion exchange resin for producing bisphenol with high percent conversion and high percent selectivity to bisphenol, especially 4,4' isopropyhdenediphenol, wherein said ion exchange resin comprising aromatic polymer having sulfonic acid group modified with at least one promoter selected from compounds shown in the structure (I), (II), (III), (IV) or its amine salt: wherein R represents hydrocarbon unit with 1 to 6 carbon atoms selected from alkyl group, alkenyl group, alkynyl group, phenyl group, or optionally hydrocarbon containing carbonyl group having 1 to 6 carbon atoms; X represents heteroatom; n is an integer number from 1 to 4.

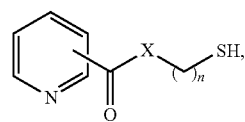

(I)

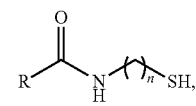

(II)

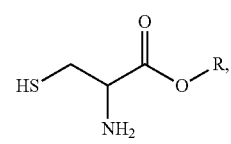

(III)

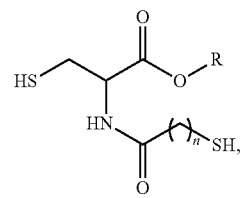

(IV)

28 Claims, No Drawings

(56) References Cited

U.S. PATENT DOCUMENTS

| | | | | |
|---|---|---|---|---|
| 4,595,704 A | * | 6/1986 | Fazio | B01J 31/10 521/31 |
| 6,372,912 B1 | * | 4/2002 | Doring | C07C 319/02 548/147 |
| 6,492,562 B1 | | 12/2002 | Ashley et al. | |

OTHER PUBLICATIONS

Baud, M. G. J. et al. "Highly Ligand Efficient and Selective N-2-(Thioethyl)picolinamide Histone Deacetylase Inhibitors Inspired by the Natural Product Psammaplin A" ChemMedChem 2013, 8, 149-156 (Year: 2013).*

Substance Record for SID 163550271 (Pubchem) PubChem Open Chemistry Database; Jun. 11, 2013; image on p. 3.

* cited by examiner

ION EXCHANGE RESIN FOR PRODUCING BISPHENOL, AND A METHOD FOR PRODUCING BISPHENOL USING SAID ION EXCHANGE RESIN

TECHNICAL FIELD

This present invention relates to an ion exchange resin for producing bisphenol, and a method for producing bisphenol using said ion exchange resin, wherein said ion exchange resin comprising aromatic polymer having sulfonic acid group modified with at least one promoter selected from compounds shown in the structure (I), (II), (III), (IV) or its amine salt:

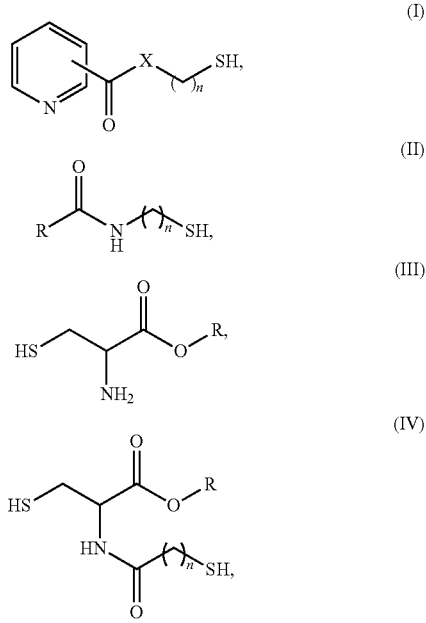

wherein
R represents hydrocarbon unit having 1 to 6 carbon atom selected from alkyl group, alkenyl group, alkynyl group, phenyl group, or optionally hydrocarbon containing carbonyl group having 1 to 6 carbon atom;
x represents heteroatom;
n is an integer number from 1 to 4.

BACKGROUND OF THE INVENTION

It is well known that bisphenol, a compound obtained from the condensation between phenol and ketone, is used primarily in a production of engineering thermoplastic, especially 4,4' isopropylidenediphenol (4,4' BPA) for polycarbonate preparation. Said reaction requires an acidic compound as a catalyst.

Inorganic acid such as sulfuric acid or hydrochloric acid can be used as the catalyst for bisphenol preparation. However, the use of inorganic acid requires additional means to neutralize such acids so as to prevent a corrosion of equipment in the process. Moreover, said acids cause undesired products, leading to a difficulty in separation and purification of product, which is the limitation for the production in industrial scale.

There has been reported that the use of ion exchange resin as a catalyst in bisphenol preparation could overcome above problems. However, said ion exchange resin always provides low activity, reaction rate, and product selectivity. Therefore, the ion exchange resin with promoter is needed, either as co-feed promoter or immobilization through ionic bond or chemical bond. Compared to the co-feed promoter, the immobilization has been widely applied in industrial scale because of less exposure and contamination of promoter during production, and no need of further process to separate promoter from obtained product.

Until now, there have been widely reported that mercaptan compound is suitable as a promoter for ion exchange resin. Although there have been widely studied to develop the ion exchange resin comprising said promoter, the catalyst results in some undesired properties such as catalyst shelf life, selectivity to bisphenol especially 4,4' isopropylidenediphenol, activity, and percent conversion.

U.S. Pat. No. 3,394,089 disclosed the improvement of catalyst for bisphenol preparation using partial neutralization of ion exchange resin by mercaptoamine compound. It was found that said mercaptoamine compound improved percent conversion and catalyst stability.

U.S. Pat. No. 4,584,416 disclosed the bisphenol preparation in the presence of ion exchange resin modified with a promoter selected from N-alkylaminoalkylmercaptan at 25 to 35% by mole. It was found that said modified ion exchange resin provided higher percent conversion and stability, comparing to general promoter, ethylmercaptan.

EP0676237 disclosed the bisphenol preparation in the presence of ion exchange resin modified with a promoter having 2 substituted groups, N,N-di-substituted mercapto alkylamine. It was found that said promoter gave higher conversion and selectivity to bisphenol, wherein 4-(dibutylamino)butane-1-thiol gave the highest bisphenol selectivity of 94%.

U.S. Pat. No. 5,075,511 disclosed the bisphenol preparation in the presence of ion exchange resin modified with a promoter selected from alkylmercaptoamine containing at least 2 alkylmercaptan branches. It was found that bis-2-(mercaptoethyl)amine gave higher 4,4' isopropylidenediphenol selectivity when compared to alkylmercaptoamine containing 1 alkylmercaptan branch, namely cysteamine.

U.S. Pat. No. 6,534,686 disclosed the bisphenol preparation in the presence of ion exchange resin modified with a promoter selected from mercaptan comprising pyridine and sulfur-protected group by functional group selected from tertiary alkyl group, ester group, and benzyl group. It was found that sulfur-protected group could increase 4,4' isopropylidenediphenol selectivity. However, percent yield of obtained 4,4' isopropylidenediphenol was relatively low.

WO2004078345 disclosed the bisphenol preparation in the presence of ion exchange resin modified with a promoter containing at least 2 sulfur groups. It was found that the promoter containing at least 2 sulfur groups could increase 4,4' isopropylidenediphenol selectivity. However, percent yield of obtained 4,4' isopropylidenediphenol was relatively low.

U.S. Pat. No. 6,825,386 disclosed an ion exchange resin that can tolerate to methanol for the bisphenol preparation. The ion exchange resin according to said invention was modified by a promoter comprising pyridinealkanethiol, aminoalkanethiol, and/or thiazolidine. It was found that said mixed promoter could increase the tolerance of methanol. However, percent conversion obtained from ion exchange resin according said invention was relatively low.

The present invention aims to prepare the ion exchange resin for producing bisphenol with high percent conversion and high percent selectivity to bisphenol, especially 4,4' isopropylidenediphenol.

SUMMARY OF INVENTION

This invention relates to ion exchange resin for producing bisphenol with high percent conversion and percent selectivity to bisphenol, especially 4,4' isopropylidenediphenol, wherein said ion exchange resin comprising aromatic polymer having sulfonic acid group modified with at least one promoter selected from compounds shown in the structure (I), (II), (III), (IV) or its amine salt:

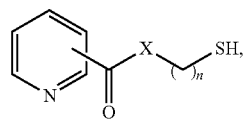
(I)

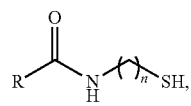
(II)

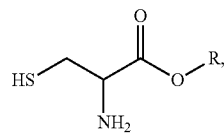
(III)

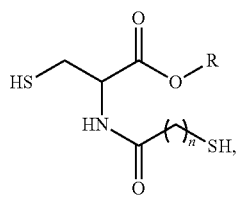
(IV)

wherein
R represents hydrocarbon unit with 1 to 6 carbon atoms selected from alkyl group, alkenyl group, alkynyl group, phenyl group, or optionally hydrocarbon containing carbonyl group having 1 to 6 carbon atoms;
x represents heteroatom;
n is an integer number from 1 to 4.

DETAILED DESCRIPTION OF THE INVENTION

Definitions

Technical terms or scientific terms used herein have definitions as understood by those having an ordinary skilled in the art, unless stated otherwise Any tools, equipment, methods, or chemicals mentioned here mean tools, equipment, methods, or chemicals commonly operated or used by those skilled in the art, unless explicated stated otherwise that they are tools, equipment, methods, or chemicals specific used in this invention.

Use of singular noun or singular pronoun with "comprising" in the claims or the specification refers to "one" and also "one or more", "at least one", and "one or more than one".

All compositions and/or methods disclosed and claimed in this invention aim to cover embodiments from any action, performance, modification, or adjustment without performing an experiment with significantly different from this invention, to obtain the result as same as the present embodiment according to person ordinary skilled in the art even not specifically stated in claims. Therefore, substitutable or similar detail to the present embodiment, including a slight modification or adjustment that is obvious by a person skilled in the art would be construed as in the scope and concept of the present invention.

Throughout this application, the term "about" is used to indicate that any value presented or showed herein may potentially vary or deviate. Such variation or deviation may result from errors of equipment, method, including variations or deviations occurred from changes in reaction condition of uncontrollable factors such as moisture and temperature.

Heteroatom means non-carbon atoms, including but not limited to nitrogen, sulfur, and oxygen.

One objective of invention is the ion exchange resin comprising aromatic polymer containing sulfonic acid group modified with a new promoter in order to be used as a catalyst for producing bisphenol.

Another objective of this invention is to use the ion exchange resin according to the invention for producing bisphenol from phenol and ketone, giving high percent conversion and high selectivity to bisphenol, especially 4,4' isopropylidenediphenol.

The following details describe the specification of the invention, and are no intended limit the scope of the invention.

The present invention related to the ion exchange resin for producing bisphenol, wherein said ion exchange resin comprising aromatic polymer containing sulfonic acid group modified with at least one promoter selected from compounds shown in the structure (I), (II), (III), (IV) or its amine salt:

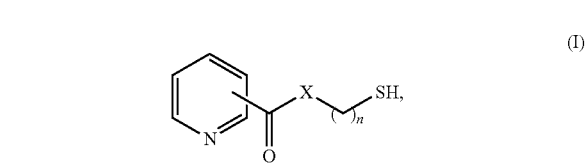
(I)

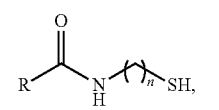
(II)

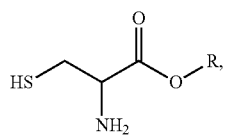
(III)

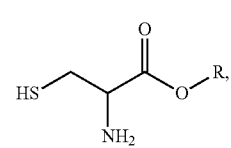
(IV)

wherein
R represents hydrocarbon unit with 1 to 6 carbon atom selected from alkyl group, alkenyl group, alkynyl group, phenyl group, or optionally hydrocarbon containing carbonyl group having 1 to 6 carbon atoms;

x represents heteroatom;

n is an integer number from 1 to 4.

Preferably, the ion exchange resin according to the invention comprising aromatic polymer containing sulfonic acid group modified with at least one promoter selected from compounds shown in the structure (V), (VI), (VII), (VIII), (IX), (X), or its amine salt:

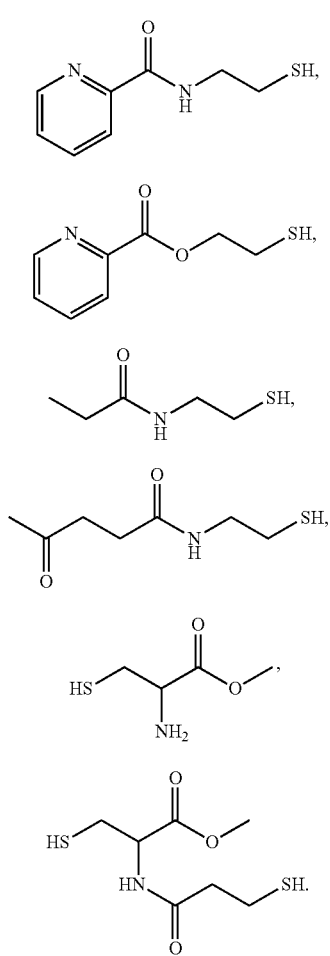

More preferably, the promoter is compound as shown in the structure (V) or its amine salt

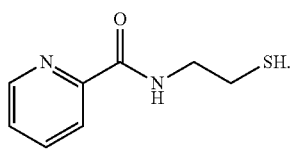

In one embodiment, said promoter further comprises aminoalkyl mercaptan which may be selected from cysteamine, 2-amino-1-propanethiol, and 3-mercaptopropylamine or its amine salt. Preferably, aminoalkyl mercaptan is cysteamine.

Most preferably, the promoter is a mixture of the amine salt of compound according to the structure (V) and the amine salt of cysteamine.

Generally, the use of promoter as amine salt form could increase the solubility of promoter during the modification of sulfonic group in aromatic polymer, wherein the amine salt may be selected from, but not limited to, hydrochloride salt, hydrobromide salt, acetate salt, formate salt, nitrate salt, phosphate salt, and perchlorate salt, preferably hydrochloride salt.

In one embodiment, aminoalkyl mercaptan or its amine salt is used in the amount of 10 to 90% by mole of total promoter, preferably 30 to 70% by mole of total promoter.

In one embodiment, the sulfonic acid group modified with promoter is 5 to 30% of total sulfonic acid group, preferably 10 to 20% of total sulfonic acid group.

In one embodiment, the sulfonic acid group is modified with promoter through ionic bond, which may be formed through nitrogen atom of said promoter and sulfonic acid group of aromatic polymer.

Generally, said modification may be performed by mixing aromatic polymer containing sulfonic acid group and, promoter, in which water or aromatic hydroxy compound is used as a solvent.

In one embodiment, the aromatic polymer containing sulfonic acid group may be selected from polystyrene having sulfonic acid group or styrene-divinylbenzene copolymer having sulfonic acid group, preferably styrene-divinylbenzene copolymer containing sulfonic acid group.

In one embodiment said styrene-divinylbenzene copolymer containing sulfonic acid group may have divinylbenzene in the amount of 1 to 10%, preferably in the amount of 1 to 4%.

In one embodiment, said aromatic polymer containing sulfonic acid group has particle size from 500 to 1500 micron, preferably from 850 to 1400 micron.

In one embodiment, the compound according to the structure (I), (II), (III) or its amine salt may be prepared by the following step:

(a) mixing monocarboxylic acid and mercapto compound in a mole ratio of monocarboxylic acid to mercapto compound from 1:1 to 1:2; and (b) adding carbodimide and basic solution into the mixture obtained from step (a).

In one embodiment, the monocarboxylic acid in step (a) may be selected from 2-pyridinecarboxylic acid, 3-pyridinecarboxylic acid, 4-pyridinecarboxylic acid, 6-methyl-2-pyridinecarboxylic acid, 5-methyl-2-pyridinecarboxylic acid, 4-methyl-2-pyridinecarboxylic acid, 3-methyl-2-pyridinecarboxylic acid, 3-ethyl-2-pyridinecarboxylic acid, propionic acid, butanoic acid, pentanoic acid, levulinic acid, and hexanoic acid, preferably 2-pyridinecarboxylic acid, 4-pyridinecarboxylic acid, or levulinic acid.

In one embodiment, the mercapto compound in step (a) is mercaptoamine or mercaptoalcohol.

In one embodiment, the mercaptoamine may be selected from cysteamine hydrochloride, 2-amino-1-propanethiol, 2-amino-1-propanethiol hydrochloride, 3-mercaptopropylamine hydrochloride, 3-amino-2-methyl-1-propanethiol, 3-amino-1-butanethiol, 3-amino-2-butanethiol, 4-amino-2-butanethiol hydrochloride, 3-amino-1-butanethiol hydrochloride, 3-amino-2,2-dimethyl-1-propanethiol, 3-amino-1-pentanethiol, 3-amino-1-pentanethiol hydrochloride, 3-amino-3-methyl-1-butanethiol, and 3-amino-3-methyl-1-butanethiol hydrochloride, preferably cysteamine hydrochloride.

In one embodiment, the mercaptoalcohol may be selected from mercaptoethanol, 3-mercaptopropanol, 4-mercaptobutanol, 2,3-mercaptopropanol, 2-mercaptobutanol, mercaptobutanol, or 3-mercapto-2-butanol, preferably mercaptoethanol.

In one embodiment, the carbodiimide in step (b) may be selected from dicyclohexylcarbodiimide, N,N'-diisopropylcarbodiimide, N-(3-dimethylaminopropyl)-N'-ethylcarbodiimide hydrochloride, N-Methyl-N'-tert-butylcarbodiimide, N-ethyl-N'-tert-butylcarbodiimide, N-cyclohexyl-N'-tert-butylcarbodiimide, and 1,3-bis(2,2-dimethyl-1,3-dioxolan-4-ylmethyl)carbodiimide, preferably N,N'-dicyclohexylcarbodiimide.

In one embodiment, the basic solution in step (b) may be selected from pyridine 4-dimethylaminopyridine, 2,4,6-trimethylpyridine, diisopropylethylamine, N-methylmorpholine, trimethylamine, and N,N-dimethylaniline, preferably 4-dimethylaminopyridine.

In one embodiment, the compound according to structure (III) or its amine may be prepared by the following step:

(a) mixing chlorinating agent and alcohol having 1 to 4 carbon atoms, wherein a volume ratio of chlorinating agent to alcohol is from 1:5 to 1:20; and (b) adding cysteine or its salt into the mixture obtained from step (a) ratio of chlorinating agent to cysteine or its salt is from 5:1 to 10:1.

In one embodiment, the chlorinating agent in step (a) may be selected from thionyl chloride, acetyl chloride, hydrochloric acid, and trimethylsilyl chloride preferably thionyl chloride.

In one embodiment, the alcohol in step (a) may be selected from methanol, ethanol, propanol, or butanol.

In another embodiment, the present invention relates to the method for producing bisphenol from phenol and ketone using the ion exchange resin according to the invention as a catalyst.

In one embodiment, the ketone may be selected from, but not limited to acetone, diethyl ketone, methyl ethyl ketone, ethylmethylkeone, isobutylmethyl ketone, cyclohexanone, and acetophenone.

In one embodiment, the phenol may be selected from, but not limited to unsubstituted phenol, alkylphenol, alkoxyphenol, naphthol, alkylnaphthol, and alkoxynaphthol.

Preferably, the ion exchange resin according to the invention is used as a catalyst in the production of bisphenol A from unsubstituted phenol and acetone by condensation reaction.

In one embodiment, the reaction condition may be adjusted to be suitable for the reaction. Normally, the mole ratio of bisphenol to acetone used in the reaction may be from 5 to 30. The reaction temperature may be operated from 40 to 120° C., preferably from 60 to 80° C. The reaction is normally operated under an atmospheric pressure.

In one embodiment, the ion exchange resin according to the invention can be used as a catalyst in several forms according to reaction system. It may be used as a slurry in batch system or as a fixed bed in continuous system.

In one embodiment, a reaction time may be in a range of 0.5 to 20 hours for in batch system and continuous system. Liquid hourly space velocity (LHSV) may be in a range of 0.5 to 10 hour$^{-1}$.

In one embodiment, the product obtained from the reaction will be separated from the catalyst, and bisphenol may be separated and purified by conventional methods such as distillation, recrystallization, or solvent washing.

The following examples are presented to further illustrate this invention without any purpose to limit the scope of the invention.

Preparation of Promoter for Preparing Ion Exchange Resin According Invention

Hydrochloride Salt of the Compound as Shown in the Structure (V)

About 5 g of 2-pyridine carboxylic acid and about 5.54 g of cysteamine hydrochloride were dissolved in about 50 mL of dichloromethane solvent under an argon atmosphere. Then, the solution mixture of about 16.7 g of N,N'-dicyclohexylcarbodiimide and about 0.99 g of 4-dimethylaminopyridine were slowly added into about 20 mL of dichloromethane solvent. Said mixture was stirred at room temperature under an argon atmosphere for about 24 hours. The obtained white solid was filtered from the obtained mixture. Then, the filtrated liquid was evaporated under vacuum. Then, it was crystallized in mixed organic solvent of dichloromethane and hexane or purified by silica column. The obtained solid was separated and dried under vacuum.

Hydrochloride Salt of the Compound as Shown in the Structure (VI)

About 5 g of 2-pyridine carboxylic acid and about 3.43 g of mercaptoethanol were dissolved in about 50 mL of dichloromethane solvent under an argon atmosphere. Then, the solution mixture of about 16.7 g of N,N'-dicyclohexylcarbodiimide and about 0.99 g of 4-dimethylaminopyridine were slowly added into about 20 mL of dichloromethane solvent. Said mixture was stirred at room temperature under an argon atmosphere for about 24 hours. The obtained white solid was filtered from obtained mixture. Then, the filtrated liquid was evaporated under vacuum and was crystallized in mixed organic solvent of dichloromethane and hexane or purified by silica column. The obtained solid was separated and dried under vacuum. Then, about 5 mL of deionized water was added into about 1 g of said obtained solid. After that about 0.6 mL of about 37% hydrochloric acid solution was slowly added into said mixture, and stirred at room temperature for about 30 min. Then, the solvent was evaporated under vacuum and the solid product was dried under vacuum.

Hydrochloride Salt of the Compound as Shown in the Structure (VII)

About 2 g of propionic acid and about 3.68 g of cysteamine hydrochloride were dissolved in about 15 mL of dichloromethane solvent under an argon atmosphere. Then, the solution mixture of about 11.4 g of N,N'-dicyclohexylcarbodiimide and about 0.66 g of 4-dimethylaminopyridine were slowly added into about 15 mL of dichloromethane solvent. Said mixture was stirred at room temperature under an argon atmosphere for about 24 hours. The obtained e solid was filtered from obtained mixture. Then, the filtrated liquid was evaporated under vacuum and was crystallized in mixed organic solvent of dichloromethane and hexane or purified by silica column. The obtained solid was separated and dried under vacuum.

Hydrochloride Salt of Compound as Shown in Structure (VIII)

About 5 g of levulinic acid and about 5.87 g of cysteamine hydrochloride were dissolved in about 20 mL of dichloromethane solvent under argon atmosphere. Then, the solution mixture of about 17.8 g of N,N'-dicyclohexylcarbodiimide and about 1.05 g of 4-dimethylaminopyridine were slowly added into about 20 mL of dichloromethane solvent. Said mixture was stirred at room temperature under an argon atmosphere for about 24 hours. The obtained white solid was filtered from obtained mixture. Then, the filtrated liquid was evaporated under vacuum and was crystallized in mixed organic solvent of dichloromethane and hexane or purified by silica column. The obtained solid was separated and dried under vacuum.

Hydrochloride Salt of Compound as Shown in Structure (IX)

About 3 mL of thionyl chloride was slowly added into about 35 mL of methanol at temperature about 0° C. under an argon atmosphere. Said mixture was stirred for about 1 hour. Then, about 1 g of cysteamine hydrochloride was added. Said mixture was stirred for about 3 hours and refluxed for about 1 hour. Then, the organic solvent was evaporated under vacuum. The obtained product was crystallized in mixed organic solvent of dichloromethane and methanol. The obtained solid was separated and dried under vacuum.

Hydrochloride Salt of Compound as Shown in Structure (X)

About 1.04 g of compound shown in structure (X) and about 0.48 g of mercapto propionic acid were dissolved in about 5 mL of N,N-dimethylformamide under an argon atmosphere. Then, the solution mixture of about 1.25 g of N,N'-dicyclohexylcarbodiimide and about 0.81 g of 4-dimethylaminopyridine were slowly added into about 10 mL of dichloromethane solvent. Said mixture was stirred at room temperature under an argon atmosphere for about 24 hours. The obtained white solid was filtered from obtained mixture. Then, the filtrated liquid was evaporated under vacuum and was crystallized in mixed organic solvent of dichloromethane and hexane or purified by silica column. The obtained solid was separated and dried under vacuum.

Preparation of Ion Exchange Resin According to the Invention

Styrene-divinylbenzene copolymer type aromatic polymer having sulfonic acid group Purolite122 (Pu122) with particle size from 850 to 1400 micron from Pulorite Co., Ltd. and Amberlyst36 (Am36) with particle size from 550 to 700 micron from Rohm and Haas Chemical Co., Ltd. were used in the preparation of ion exchange resin according to the invention.

The aromatic polymer having sulfonic acid group modified with various promoters in amounts and percentages according to Table 1 were prepared by the following method.

The promoter was dissolved in about 20 mL of deionized water (in the amount as shown in Table 1). Then, said solution was added in to about 20 g of styrene-divinylbenzene copolymer suspended in about 40 mL of deionized water. The mixture was stirred at a room temperature for about 1 hour. After stirring, the obtained mixture was packed in the column and washed with deionized water at a flow rate about 1 mL/min until the pH of washing liquid was about 6.5. The obtained solid was tested for residue sulfonic group by titration method with sodium hydroxide solution in order to measure sulfonic acid group ($SO_3H$) before and after aromatic polymer modification. The percentage of sulfonic acid group modified with promoter could be calculated from the following equation.

$$\text{percentage of sulfonic acid group modified with promoter} = \frac{\text{mole of SO3H before modification} - \text{mole of SO3H } aftermodification}{\text{mole of SO3H before modification}} \times 100$$

Testing of Bisphenol Production

The ion exchange resin according to the invention was used a catalyst for testing bisphenol production performance by the following method.

Prior to use, the ion exchange resin was dehydrated by contacting about 10 g of ion exchange resin with about 100 g of phenol at the temperature about 60 to 70° C. for about 15 min. This method was performed in 3 times. About 3 g of obtained ion exchange resin was added in a 250 mL 3-neck flask equipped with a condenser. Then, about 90 g of phenol was added and heated at the temperature of about 70° C. Then, about 4.27 g of acetone was added. The reaction was operated until about 1 hour.

The followings are examples for testing of product compositions obtained from the ion exchange resin according to the invention, wherein testing methods and equipment are general methods and equipment and not intended to limit the scope of the invention.

The remaining acetone from the reaction was tested by gas chromatography (Shimadzu 17A-GC) equipped with HP-PLOT/Al2O3 "S" deactivated capillary column. The column temperature was set in order to separate compositions. The temperature was set at about 40° C. for about 10 min at the beginning. Then, the temperature was raised at a linear rate to about 195° C. and maintained for about 30 min.

The product compositions were tested by High Performance Liquid Chromatography (Shimadzu LC-20AD) equipped with Phenomenex Gemini-NX 5µ C18 column. Water and acetonitrile at 1:1 ratio by volume was used as a mobile phase with a flow rate of 1 mL/min.

The % acetone conversion and % selectivity of 4,4' isopropylidenediphenol (4,4' BPA) were calculated from the following equations.

$$\% \text{ acetone conversion} = \frac{\text{mole of acetone reacted}}{\text{mole of initial acetone}} \times 100$$

$$\% \text{ selectivity of 4,4' isopropylidenediphenol} = \frac{\text{mole of 4,4' isopropylidenediphenol}}{\text{mole of 4,4' isopropylidenediphenol} + \text{mole of 2,4' isopropylidenediphenol}}$$

Table 1 shows % acetone conversion and 5 selectivity of 4,4'isopropylidenediphenol of ion exchange resins

| Sample | Styrene-divinylbenzene copolymer type | Promoter | % Sulfonic acid group modified with promoter | % acetone conversion | % selectivity of 4,4' isopropylidene diphenol |
|---|---|---|---|---|---|
| Comparative sample 1 | Pu122 | — | — | 23.2 | 84.7 |
| Comparative sample 2 | Am36 | — | — | 17.7 | 90.1 |

-continued

| Sample | Styrene-divinylbenzene copolymer type | Promoter | % Sulfonic acid group modified with promoter | % acetone conversion | % selectivity of 4,4' isopropylidene diphenol |
|---|---|---|---|---|---|
| Comparative sample 3 | Pu122 | cysteamine hydrochloride 0.21 g | 10 | 36.5 | 96.2 |
| Sample A1 | Pu122 | hydrochloride salt of compound with structure (V) 0.40 g | 10 | 35.7 | 97 |
| Sample A2 | Am36 | hydrochloride salt of compound with structure (V) 1.02 g | 10 | 27.8 | 97.3 |
| Sample A3 | Pu122 | hydrochloride salt of compound with structure (V) 0.80 g | 20 | 32.4 | 97.1 |
| Sample B | Pu122 | hydrochloride salt of compound with structure (VI) 0.34 g | 10 | 20.6 | 94.2 |
| Sample C | Pu122 | hydrochloride salt of compound with structure (VII) 0.31 g | 10 | 23.2 | 95.3 |
| Sample D | Pu122 | hydrochloride salt of compound with structure (VIII) 0.39 g | 10 | 31.8 | 93.5 |
| Sample E | Pu122 | hydrochloride salt of compound with structure (IX) 0.32 g | 10 | 28.4 | 96.6 |
| Sample F | Pu122 | hydrochloride salt of compound with structure (X) 0.48 g | 10 | 25.2 | 91.3 |
| Sample G1 | Pu122 | cysteamine hydrochloride 0.06 g + hydrochloride salt of compound with structure (V) 0.28 g | 10 | 42.5 | 96.9 |
| Sample G2 | Pu122 | cysteamine hydrochloride 0.11 g + hydrochloride salt of compound with structure (V) 0.20 g | 10 | 49.0 | 96.7 |
| Sample G3 | Pu122 | cysteamine hydrochloride 0.15 g + hydrochloride salt of compound with structure (V) 0.12 g | 10 | 48.4 | 97.4 |
| Sample G4 | Pu122 | cysteamine hydrochloride 0.29 g + hydrochloride salt of compound with structure (V) 0.24 g | 10 | 42.0 | 97.1 |

From Table 1, when comparing the comparative samples, and samples A1 to A3 and B to F according to the invention which 1 promoter was used in the preparation, it can be found that the ion exchange resin according to the invention which has sulfonic acid group modified by hydrochloride salt of the compound according to the structure (V), (VI), (VII), (VIII), (IX), and (X) has higher percent acetone conversion and percent selectivity of 4,4' isopropylidenediphenol. The ion exchange resin having sulfonic acid group modified by hydrochloride salt of compound according to structure (V) results in the highest percent selectivity of 4,4' isopropylidenediphenol.

Moreover, when comparing the comparative example, sample A1 containing 1 promoter and sample G1 to G3 containing hydrochloride salt of compound according to the structure (V) and cysteamine hydrochloride with the same percent of sulfonic acid group modified by promoter, it can be found that the use of said 2 promoters yields greatly higher percent acetone conversion.

From the results above, it can be said that the ion exchange resin according to the invention gives high conversion and high selectivity to bisphenol, especially 4,4' isopropylidenediphenol as being stated in the objective of this invention.

BEST MODE OF THE INVENTION

Best mode of the invention is as provided in the description of the invention.

The invention claimed is:

1. An ion exchange resin for producing bisphenol comprising aromatic polymer having a sulfonic acid group modified with at least one promoter selected from the group consisting of compounds shown in the structure (I), (IV) and amine salt thereof:

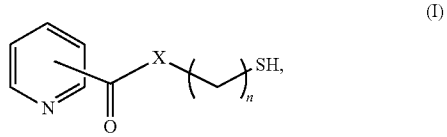

-continued

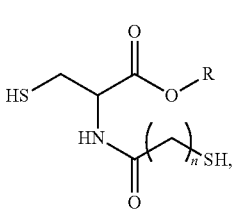
(IV)

wherein
R represents hydrocarbon unit having 1 to 6 carbon atoms selected from the group consisting of alkyl group, alkenyl group, alkynyl group, phenyl group, and a hydrocarbon containing carbonyl group having 1 to 6 carbon atoms;
x represents heteroatom;
n is an integer number from 1 to 4.

2. The ion exchange resin according to claim 1, wherein at least one promoter is selected from the group consisting of compounds shown in the structure (V), (VI), (X), and amine salt thereof:

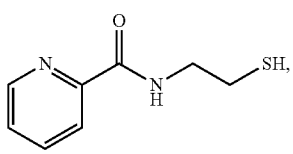
(V)

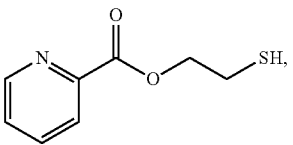
(VI)

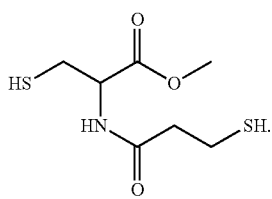
(X)

3. The ion exchange resin according to claim 1, wherein the promoter is a compound as shown in the structure (V) or amine salt thereof

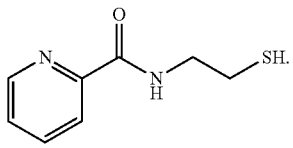
(V)

4. The ion exchange resin according to claim 1, wherein the promoter further comprises aminoalkyl mercaptan or amine salt thereof.

5. The ion exchange resin according to claim 4, wherein aminoalkyl mercaptan is cysteamine.

6. The ion exchange resin according to claim 4, wherein aminoalkyl mercaptan or its amine salt is used in the amount of 10 to 90% by mole of total promoter.

7. The ion exchange resin according to claim 6, wherein aminoalkyl mercaptan or its amine salt is used in the amount of 30 to 70% by mole of total promoter.

8. The ion exchange resin according to claim 1, wherein the sulfonic acid group modified with promoter is 5 to 30% of total sulfonic acid group.

9. The ion exchange resin according to claim 8, wherein the sulfonic acid group modified with promoter is 10 to 20% of total sulfonic acid group.

10. The ion exchange resin according to claim 1, wherein the sulfonic acid group is modified with promoter through ionic bond.

11. The ion exchange resin according to claim 1, wherein the aromatic polymer containing sulfonic acid group is selected from the group consisting of polystyrene having sulfonic acid group and styrene-divinylbenzene copolymer having sulfonic acid group.

12. The ion exchange resin according to claim 11, wherein the aromatic polymer containing sulfonic acid group is styrene-divinylbenzene copolymer having sulfonic acid group.

13. The ion exchange resin according to claim 12, wherein the styrene- divinylbenzene copolymer having sulfonic acid group has divinylbenzene in the amount of 1 to 10%.

14. The ion exchange resin according to claim 13, wherein the styrene- divinylbenzene copolymer having sulfonic acid group has divinylbenzene in the amount of 1 to 4%.

15. The ion exchange resin according to claim 1, wherein the aromatic polymer containing sulfonic acid group has particle size from 500 to 1500 micron.

16. The ion exchange resin according to claim 15, wherein the aromatic polymer having sulfonic acid group has particle size from 850 to 1400 micron.

17. The ion exchange resin according to claim 1, wherein the compound according to structure (I) or amine salt of said compound is prepared by the following step:
(a) mixing monocarboxylic acid and mercapto compound in a mole ratio of monocarboxylic acid to mercapto compound from 1:1 to 1:2; and
(b) adding carbodiimide and basic solution into the mixture obtained from step (a).

18. The ion exchange resin according to claim 17, wherein the mercapto compound in step (a) is mercaptoamine or mercaptoalcohol.

19. The ion exchange resin according to claim 18, wherein the mercaptoamine is selected from the group consisting of cysteamine hydrochloride, 2-amino-1-propanethiol, 2-amino-1-propanethiol hydrochloride, 3-mercaptopropylamine hydrochloride, 3-amino-2-methyl-1-propanethiol, 3-amino-1-butanethiol, 3-amino-2-butanethiol, 4-amino-2-butanethiol hydrochloride, 3-amino-1-butanethiol hydrochloride, 3-amino-2,2-dimethyl-1-propanethiol, 3-amino-1-pentanethiol, 3-amino-1-pentanethiol hydrochloride, 3-amino-3-methyl-1-butanethiol, and 3-amino-3-methyl-1-1-butanethiol hydrochloride.

20. The ion exchange resin according to claim 19, wherein the mercaptoamine is cysteamine hydrochloride.

21. The ion exchange resin according to claim 18, wherein the mercaptoalcohol is selected from the group consisting of mercaptoethanol, 3-mercaptopropanol, 4-mercaptobutanol, 2,3-mercaptopropanol, 2-mercaptobutanol, 3-mercaptobutanol, and 3-mercapto-2-butanol.

22. The ion exchange resin according to claim 21, wherein the mercaptoalcohol is mercaptoethanol.

23. The ion exchange resin according to claim 17, wherein the carbodiimide in step (b) is selected from the group consisting of N,N'- dicyclohexylcarbodiimide, N,N'-diisopropylcarbodiimide, N-(3-dimethylaminopropyl)-N'- ethyl-carbodiimide hydrochloride, N-Methyl-N'-tert-butyl carbodiimide, N-ethyl-N'-tert- butylcarbodiimide, N-cyclohexyl-N'-tert-butylcarbodiimide, and 1,3-bis(2,2-dimethyl-1,3-dioxolan-4-ylmethyl)carbodiimide.

24. The ion exchange resin according to claim 23, wherein the carbodiimide is N,N'-dicyclohexylcarbodiimide.

25. The ion exchange resin according to claim 17, wherein the basic solution in step (b) is selected from the group consisting of pyridine, 4- dimethylaminopyridine, 2,4,6-trimethylpyridine, diisopropyl ethylamine, N- methylmorpholine, trimethylamine, and N,N-dimethylaniline.

26. The ion exchange resin according to claim 25, wherein the basic solution in step (b) is 4-dimethylaminopyridine.

27. A method for producing bisphenol from phenol and ketone using the ion exchange resin, wherein the ion exchange resin comprising aromatic polymer having a sulfonic acid group modified with at least one promoter selected from the group consisting of compounds shown in the structure (I), (III), (IV) and amine salt thereof:

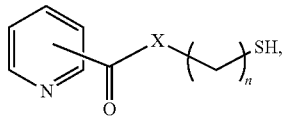 (I)

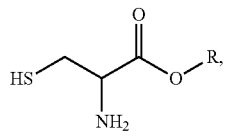 (III)

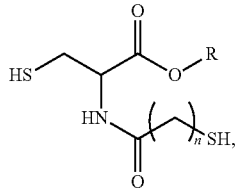 (IV)

wherein R represents hydrocarbon unit having 1 to 6 carbon atoms selected from the group consisting of alkyl group, alkenyl group, alkynyl group, phenyl group, and a hydrocarbon containing carbonyl group having 1 to 6 carbon atoms;

x represents heteroatom;

n is an integer number from 1 to 4.

28. The method according to claim 27, wherein the phenol is unsubstituted phenol, the ketone is acetone, and the bisphenol is bisphenol A.

* * * * *